United States Patent
Hoover

(10) Patent No.: US 7,364,674 B1
(45) Date of Patent: Apr. 29, 2008

(54) CORNEAL IMPLANTS PRODUCED BY IRRADIATION OF POLYMER FILMS

(75) Inventor: Brian G. Hoover, Albuquerque, NM (US)

(73) Assignee: Advanced Optical Technologies, Inc., Tijeras, NM (US)

( * ) Notice: Subject to any disclaimer, the term of this patent is extended or adjusted under 35 U.S.C. 154(b) by 139 days.

(21) Appl. No.: 10/625,769

(22) Filed: Jul. 23, 2003

Related U.S. Application Data

(60) Provisional application No. 60/397,906, filed on Jul. 23, 2002.

(51) Int. Cl.
*B29D 11/00* (2006.01)

(52) U.S. Cl. ............. 264/1.36; 264/488; 623/5.16

(58) Field of Classification Search .......... 264/1.36, 264/1.37, 1.38, 488; 623/5.16
See application file for complete search history.

(56) References Cited

U.S. PATENT DOCUMENTS

| | | | |
|---|---|---|---|
| 4,409,258 A | | 10/1983 | Feurer et al. |
| 4,450,593 A | * | 5/1984 | Poler ............ 623/6.4 |
| 4,655,774 A | | 4/1987 | Choyce |
| 4,732,715 A | * | 3/1988 | Bawa et al. .......... 264/1.36 |
| 4,744,647 A | | 5/1988 | Meshel et al. |
| 5,061,057 A | | 10/1991 | Kumakura et al. |
| 5,331,132 A | * | 7/1994 | Freeman et al. ...... 219/121.69 |
| 5,713,957 A | * | 2/1998 | Steele et al. ......... 623/5.16 |
| 6,102,946 A | | 8/2000 | Nigam |
| 6,280,469 B1 | | 8/2001 | Terry et al. |
| 6,361,560 B1 | | 3/2002 | Nigam |
| 6,874,886 B2 | | 4/2005 | Miller et al. |
| 2001/0018612 A1 | | 8/2001 | Carson et al. |

FOREIGN PATENT DOCUMENTS

| | | | |
|---|---|---|---|
| JP | 58-153326 | * | 9/1983 |
| JP | 3-57629 | * | 3/1991 |

OTHER PUBLICATIONS

Wolf, Stanley PH.D. and Tauber, Richard N. PH.D., "Silicon Processing for the VLSI Era, vol. 1: Process Technology," Book, 1st ed., Lattice Press (Sunset Beach, California), p. 430-437, (Feb. 8, 1986).

(Continued)

*Primary Examiner*—Mathieu D. Vargot
(74) *Attorney, Agent, or Firm*—Janeen Vilven-Doggett; Peacock Myers, P.C.

(57) ABSTRACT

The corneal implant of the current invention takes the general form of a thin, transparent, flexible, porous, biocompatible film of suitable polymer material. The implant is sufficiently porous, the porosity being imparted by the film being irradiated to produce tracks and the material in those tracks being subsequently removed through an etching process, to allow the adequate flow of gaseous and tissue fluid components through the film. Specific embodiments of the invention are achieved by the addition of features to the general form. The embodiment applicable to corneal reshaping features a surface relief pattern in the implant. The artificial iris embodiment features an imprinted partly to fully opaque or partially reflective annular iris pattern of selected inner and outer diameters.

10 Claims, 6 Drawing Sheets

OTHER PUBLICATIONS

Ziegler, J.F.; Biersack, J.P., Littmark, U., "The Stopping and Range of Ions in Solids," Book, Pergamon Press (U.S.A, U.K., Canada, Australia, Federal Republic of Germany), p. 109-110, 2, (Feb. 8, 1985).

Ferain, E.and Legras, R., "Track-etched membrane: dynamics of pore formation," Journal, Elsevier Science B.V. (North Holland), No. B84, p. 331-336, (Feb. 8, 1994).

Okuyama, Y; Hashimoto, T.; Koguchi, T., "High Dose Ion Implantation into Photoresist," Journal, J. Electrochem. Soc. (Japan), vol. 125 (No. 8), p. 1293-1298, (Aug. 8, 1978).

Valiev, K.A.; Velikov, L.V.; Dushenkov, S.D., "Pore formation in PMMA during x-ray exposure," Journal, Sov. Phys. Tech. Phys. (USSR), vol. 32 (No. 7), p. 862-863, (Feb. 8, 1988).

Orvek, Kevi J.; Huffman, Craig, "Carbonized Layer Formation in Ion Implanted Photoresist Masks," Journal, Elsevier Science Publishers BV (North Holland, Amsterdam), vol. B (No. 7/8), p. 501-506, (Feb. 8, 1985).

Hicks, C. et al., "Development and Clinical Assessment of an Artificial Cornea," Journal, Progress in Retinal and Eye Research, Elsevier Science Ltd. (Great Britain), vol. 19 (No. 2), p. 149-170 (2000).

Trautman, C., et al., "Etching threshold for ion tracks in polyimide," Journal, Nuclear Instruments and Methods in Physics Research B, Elsevier Science B.V. (North Holland, Amsterdam), vol. B (No. 115), p. 429-433 (1996).

Virk, H.S., et al., "Effects on insulators of swift-heavy-ion irradiation: ion-track technology," Journal, J. Phys. D: Appl. Phys., IOP Publishing Ltd. (UK), vol. 31, p. 3139-3145, (1998).

Yashar, Alyson G., "Artificial iris device may reduce glare," Magazine, Opthamalogy Times, Advanstar Communications, Inc., (Sep. 15, 2000).

* cited by examiner

CORNEAL IMPLANTS PRODUCED BY IRRADIATION OF POLYMER FILMS

CROSS REFERENCE TO RELATED APPLICATION

This application is a continuation-in-part of provisional application Ser. No. 60/397,906, filed Jul. 23, 2002, the priority of which is claimed and the subject matter of which is incorporated by reference.

FIELD OF THE INVENTION

The invention relates generally to the art of ophthalmic devices designed to correct or improve vision. More specifically the invention relates to ophthalmic devices incorporated in polymer films designed for implantation into the cornea. These ophthalmic devices are fabricated using novel techniques of ion and photon irradiation of polymer films. In one version the invention relates to an ophthalmic device to replace or augment the natural iris of the eye. However, the invention also relates to other ophthalmic devices fabricated using similar techniques, including corneal implants designed to modify the curvature of the cornea in a manner similar to that of intracorneal lenses and intrastromal corneal rings.

BACKGROUND

Synthetic corneal implants are applicable to a wide range of ophthalmic conditions. In comparison with competing treatment options, corneal implants frequently offer the advantages of relatively unobtrusive surgery, rapid patient recovery, fewer complications, and reversibility.

Polymers have become the preferred materials for the fabrication of corneal implants because they can be made to satisfy the critical requirements of biocompatibility, optical clarity, flexibility and durability in sufficiently thin films. The biocompatibility of a corneal implant is reliant on a porosity or permeability sufficient for the flow of gaseous molecules and tissue fluid components through the implant. Inadequate flow will result in corneal tissue necrosis. Hydrogel polymers may be intrinsically permeable and are used for the fabrication of certain corneal implants. Certain acrylic polymers that are not intrinsically permeable may be perforated by a focused laser beam to produce a permeable material suitable for use as a corneal implant. Irradiation of polymers with high-energy ions can generate pores along individual ion tracks thereby producing a permeable material suitable for use as a corneal implant, although ion irradiation of polymers has previously not been applied for this purpose.

The keratoprosthesis (artificial cornea) may be used as an alternative to a corneal transplant in patients affected by corneal disease or trauma. A recently approved keratoprosthesis is formed of the hydrogel poly 2-(hydroxymethacrlyate) (PHEMA) in a permeable opaque skirt bound to a non-permeable transparent pupillary region (Hicks, et. al., Prog. Retinal Eye Res. 19(2), 149-70, 2000). Corneal implants may also serve to correct or mitigate ophthalmic conditions not associated with the cornea itself. Mild myopia or nearsightedness can be corrected through implantation of intrastromal corneal rings (ICRs), which effectively flatten or decrease the curvature of the cornea. ICRs are typically made of the non-permeable acrylic poly(methylmethacrylate) (PMMA), of which intraocular lenses are also made. ICRs are in the shape of two semi-circular segments or crescents that are implanted in the cornea concentric with the pupil. The projected area of the ICRs on the cornea is sufficiently small that tissue fluid components flow around the implants and tissue necrosis does not occur. Hyperopia or farsightedness can be corrected through implantation of permeable hydrogel intracorneal lenses. The water content of hydrogels is nearly 80% by volume, which necessitates implants of this material of at least 30 microns thick to provide durability. A corneal implant may also incorporate an artificial iris, which is applicable to the treatment of several ophthalmic conditions, including replacement of a damaged iris, augmentation of an absent or incomplete iris, augmentation of an iris for the purpose of increasing opacity or changing color, and augmentation of an iris for the purpose of refractive-error compensation.

Each form of corneal implant subsumed by the present invention is designed to be implanted into the subject eye using techniques and instrumentation from the field of ophthalmic surgery, as for example described by Choyce for the placement of an artificial iris.

Certain disadvantages of previously disclosed embodiments of corneal implants are overcome by the current invention. In its most general embodiment the current invention combines controlled permeability, which is usually associated with hydrogels, with the optical clarity, flexibility, and durability of non-hydrated acrylic polymers. The corneal implants of the present invention therefore have the potential to serve as lamellar keratoprostheses whereas hydrogel implants are currently limited to full-thickness keratoprostheses. In the application of corneal reshaping the implants of the current invention are thinner than hydrogel alternatives and provide greater control over corneal reshaping than ICRs, in particular the use of asymmetric reshaping to correct for astigmatism. In the incorporation of an artificial iris in a corneal implant the current invention compares favorably with previously disclosed devices. The silicone annular mesh described by Terry and Ousley is relatively thick (around 200 microns) and has a central hole in the pupil region, which limits its placement in the cornea due to dimpling that may occur in the cornea over the hole in the pupil region and cause refractive errors. Therefore the artificial iris of Terry and Ousley must be placed deeper in the eye using a surgical procedure that requires major intrusion into the eye and a prolonged recovery period for the patient. These same disadvantages occur with the recently developed annular Dacron meshes, although these devices are ten times thinner at around 20 microns. An artificial iris has also been produced in the form of a thin graphitic annulus, which, due to brittleness, suffers from frequent fragmentation during surgical handling.

SUMMARY OF THE INVENTION

The corneal implant of the current invention takes the general form of a thin (typically 5-10 micron), transparent, flexible, porous, biocompatible film of suitable polymer material, for example poly-methylmethacrylate (PMMA). The implant is sufficiently porous to allow the adequate flow of gaseous and tissue fluid components through it. Specific embodiments of the invention are achieved by the addition of features to the general form. The embodiment applicable to corneal reshaping features a surface relief pattern in the implant. The artificial iris embodiment features an imprinted partly to fully opaque or partially reflective annular iris pattern of selected inner and outer diameters. These specific embodiments are described in more detail in subsequent paragraphs, with the artificial iris embodiment taken as an example.

The polymer film that constitutes the corneal implant of the current invention may be in an arbitrary shape with a boundary that encloses the active or optical pupillary core. The pupillary core is defined as the region of the implant through which light that contributes to vision passes or would pass in the absence of the implant. Any portion of the film external to the pupillary core constitutes the skirt of the device. The skirt may serve as a functional component to orient or anchor the implant in the eye, or it may serve as a process component to facilitate fabrication of the implant, in which case it is trephinated from the pupillary core at the appropriate processing stage.

The porosity of the corneal implant of the current invention is imparted to the polymer film by an irradiation and subsequent etching process that form a branching network of pores, an adequate fraction of which connect the anterior and posterior surfaces of the implant to allow for adequate gaseous and tissue fluid flow through it. The radiation source for pore formation can be either an x-ray or an ion source that produces radiation with either a collimated or a diffuse propagation direction. The radiation may be in the form of a confined beam that is raster-scanned over the film. Regions of the film may be fully or partially shielded from the radiation that generates the pores, and during irradiation with a collimated beam the film may be variably tilted to change the radiation incidence angle.

The specialized features of the specific embodiments of the current invention are also imparted to the polymer film through irradiation processes that utilize photon or ion sources. Optical or ion beam lithography is utilized for the production of patterned surface relief structures and ion implantation is utilized for the production of patterned opacity in the implants. Laser irradiation is utilized for the production of reflectivity patterned both spatially and spectrally. Each irradiation process is specified based on knowledge of its effects on the polymer film that constitutes the corneal implant. The ion irradiation is characterized by parameters including but not limited to ion species, ion energy, and dose, and the optical or laser irradiation is characterized by parameters including but not limited to illumination angle, wavelength, power, and exposure time.

The specific embodiment of the current invention that features an artificial iris is used as an example for the process description. The artificial iris itself is described in two embodiments, one that features an opaque iris and one that features a partially reflective iris. The artificial iris is sufficiently thin and without a hole in the pupillary core, which permits its relatively unobtrusive placement in the cornea. It is additionally flexible and durable because the absorptive or reflective layer that forms the annular iris pattern is buried within the film. The embodiment of the artificial iris that features a partially reflective iris does not impair vision in low-light settings as do all artificial iris forms that feature an opaque iris, because in this embodiment of the current invention only a narrow, pre-selected color-band is reflected while all other colors are transmitted to provide adequate light for vision in low-light settings. In the embodiment of the artificial iris that features an opaque iris, the annular iris pattern is produced by ion irradiation over an annular portion of the film. The annular irradiation pattern is defined either by a protective layer that is deposited directly onto the film in the form of a circular disk to shield the central pupil region from exposure, or by an annular stencil mask that is mounted between the ion source and the film, typically in close proximity to the latter. By this ion-irradiation process the opaque iris pattern is produced as a buried, optically absorptive layer in the polymer film. In the embodiment of the artificial iris that features a partially reflective iris the annular iris pattern is produced by laser irradiation in a flood-beam format through an annular shadow mask in close proximity to the film and with a mirror located behind the film on the side opposite the laser source. By this laser-irradiation process a reflective diffraction grating that selectively reflects certain colors of light is produced in the iris pattern.

DETAILED DESCRIPTION OF THE INVENTION

Figure 1:
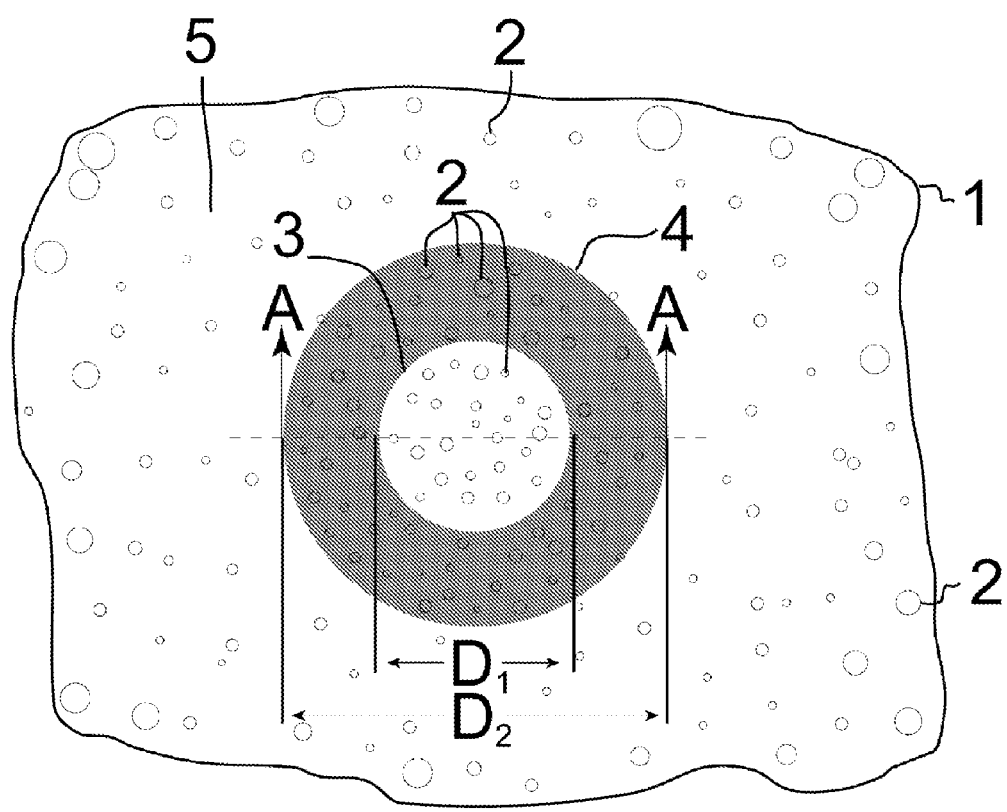
FIG. 1 is a frontal view of an artificial iris produced in accordance with a particular embodiment of the current invention.
Figure 2:
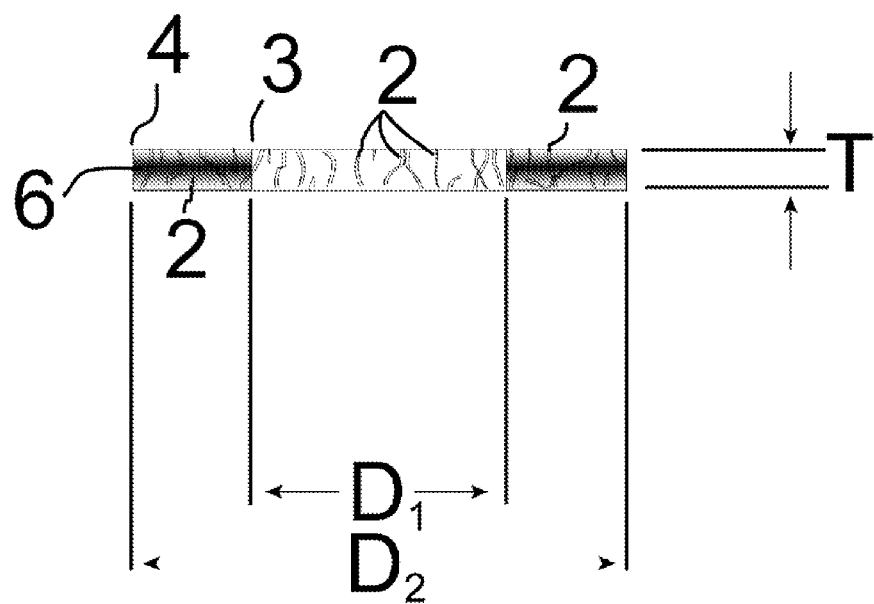
FIG. 2 is a cross-sectional view taken generally along the line A-A in FIG. 1.
Figure 3:
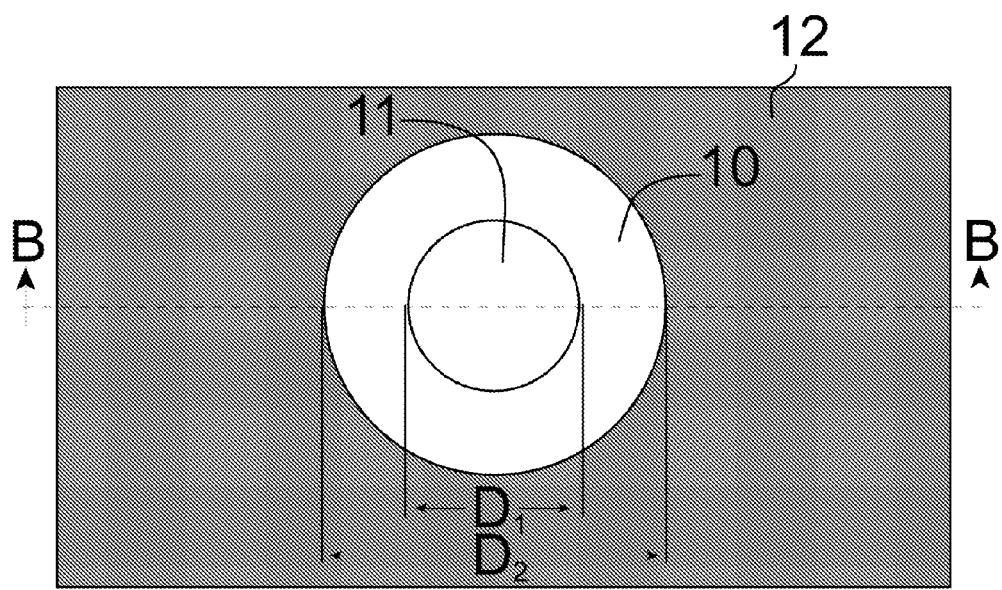
FIG. 3 is a frontal view of a surface-relief polymer structure produced by optical or ion beam lithography in the fabrication of the artificial iris embodiment of the current invention.
Figure 4:
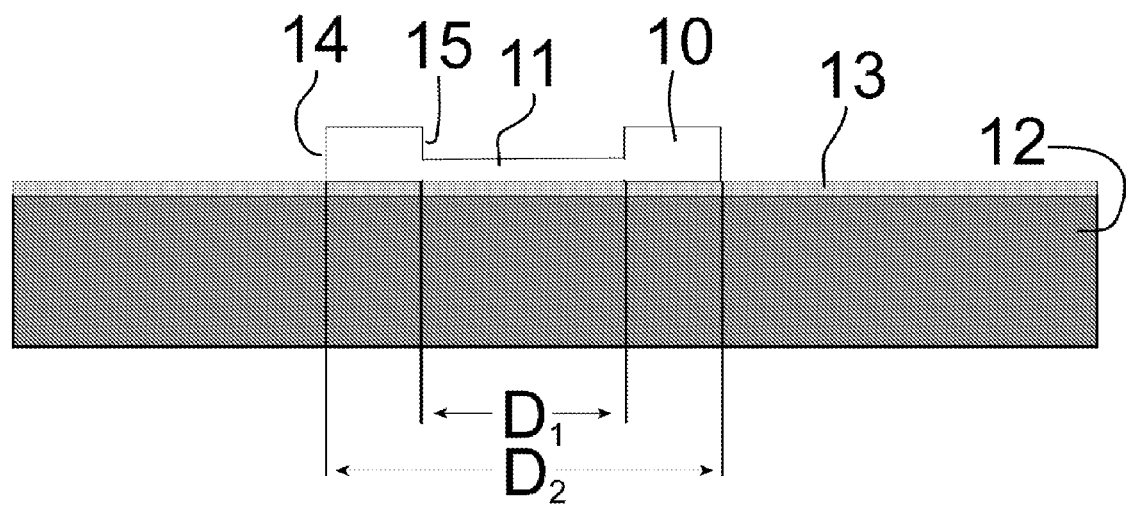
FIG. 4 is a cross-sectional view of the structure in FIG. 3 taken generally along the line B-B in FIG. 3.
Figure 5:
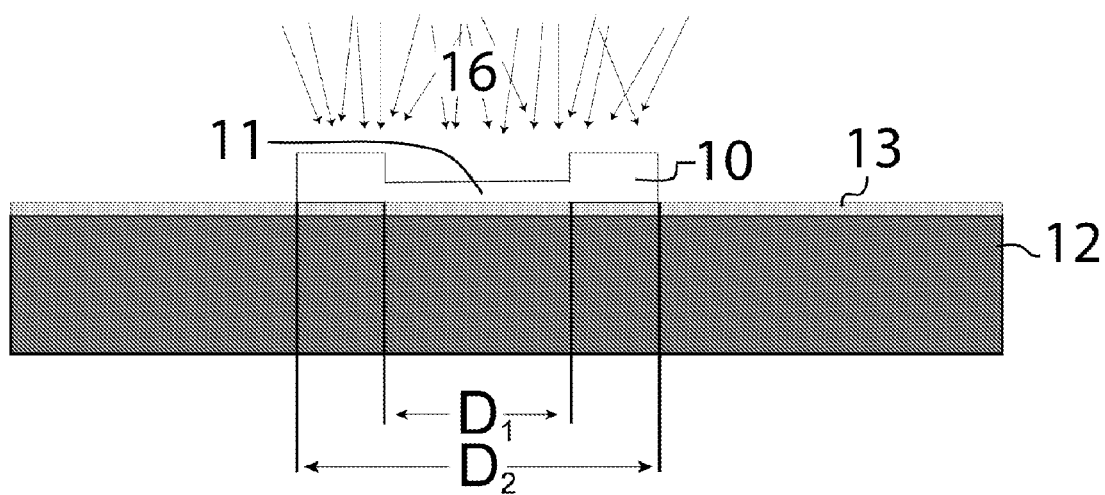
FIG. 5 is a view of the structure of FIG. 4 under uniform, diffuse ion or x-ray irradiation.
Figure 6:
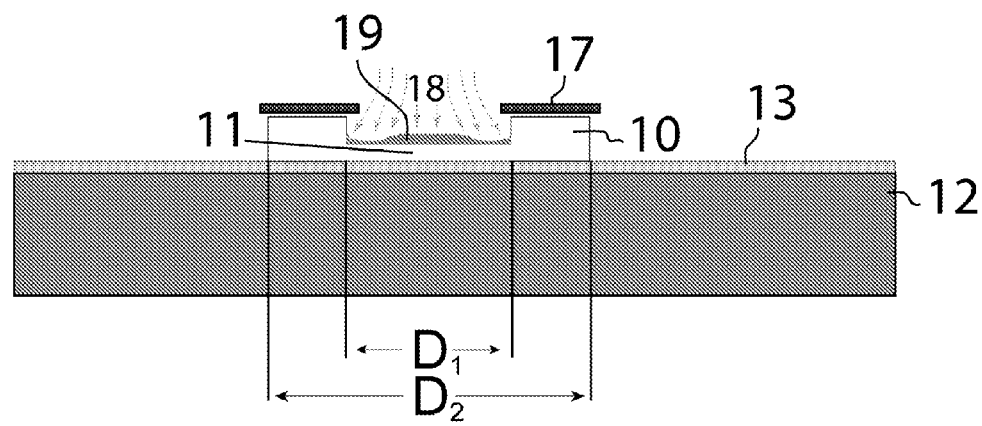
FIG. 6 is a view of the process of deposition of a protective layer onto the structure of FIG. 4 in the fabrication of the artificial iris embodiment of the current invention.
Figure 7:
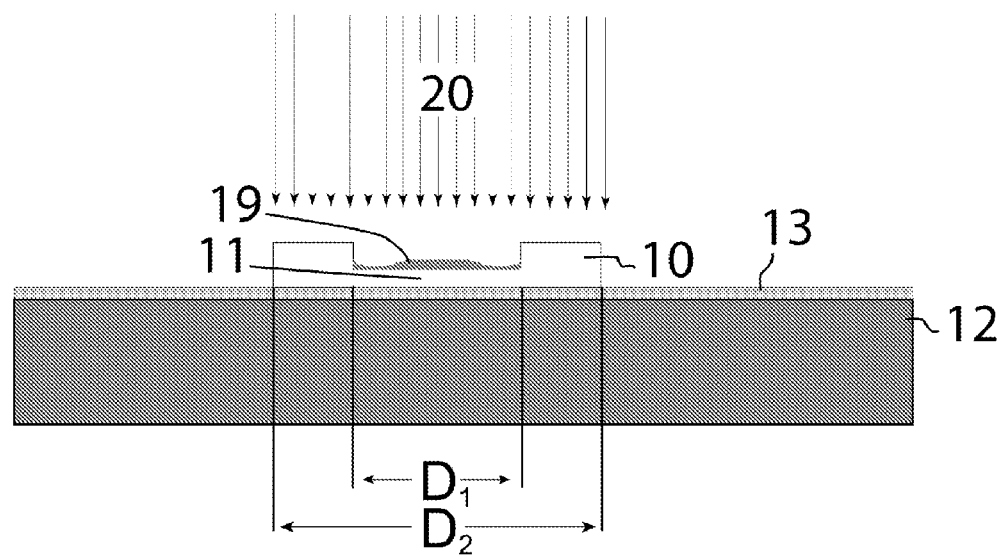
FIG. 7 is a view of the structure of FIG. 4, including the protective layer produced as in FIG. 6, under uniform, directed ion irradiation in the fabrication of the artificial iris embodiment of the current invention.
Figure 8:
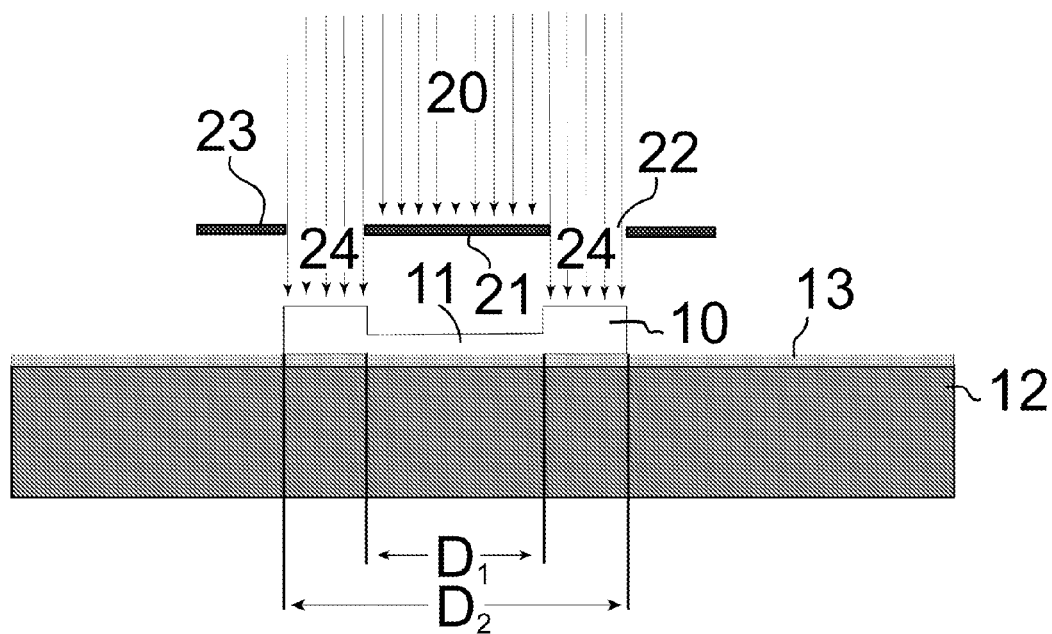
FIG. 8 is a view of the structure of FIG. 4 under directed ion irradiation through an annular stencil mask in the fabrication of the artificial iris embodiment of the current invention.
Figure 9:
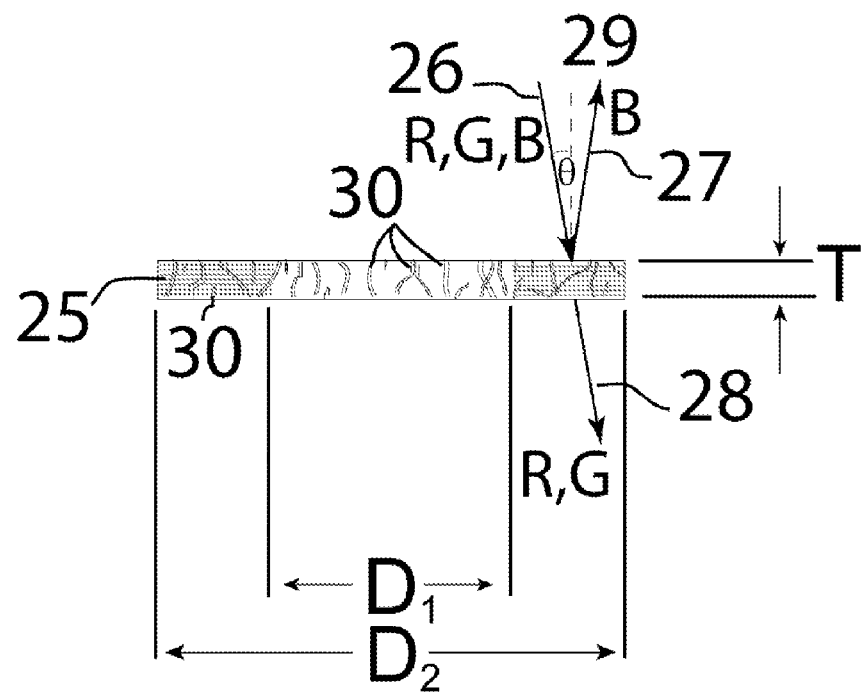
FIG. 9 is a cross-sectional view taken similarly to that of FIG. 2 of an artificial iris produced in accord with an alternative embodiment of the current invention, including a schematic representation of the spectral reflection and transmission properties of same.
Figure 10:
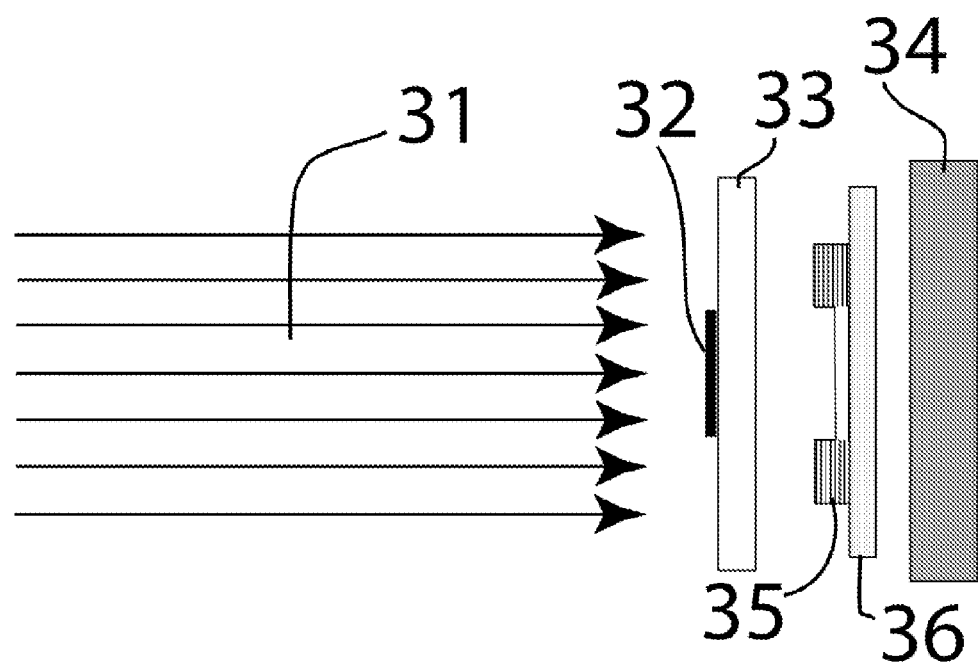
FIG. 10 is a schematic diagram of a laser irradiation configuration utilized in the second embodiment of the artificial iris embodiment of the current invention.

The product and process of the invention are now described in detail with reference to the drawings. A single specialized embodiment of the invention can serve to illustrate both the general features common to all embodiments of the invention and the features peculiar to that specialized embodiment. The artificial iris embodiment of the invention is therefore described, which itself has two embodiments. FIGS. 1-2 depict the product of the first embodiment of the artificial iris. FIGS. 3-5 depict process stages in the fabrication of the artificial iris that are common in some form to all embodiments of the corneal implant. FIGS. 6-8 depict process stages specific to the fabrication of the first embodiment of the artificial iris, and FIGS. 9-10 depict the product and specialized process of the second embodiment of the artificial iris.

The product of the first embodiment of the artificial iris is illustrated from a frontal view in FIG. 1. The artificial iris is in the form of a polymer film of arbitrary shape, bounded by the smooth edge 1, into which an absorptive or partially reflective annulus of outer diameter $D_2$ and inner diameter $D_1$ is imprinted. The polymer from which the artificial iris is made is a transparent, flexible, biocompatible material such as, but not limited to, poly(methylmethacrylate) (PMMA) or polyimide (PI). The diameters $D_1$ and $D_2$ of the iris pattern are selected to produce the desired optical effect when the artificial iris is implanted in the subject eye, although the inner diameter $D_1$ is generally no smaller than 1 millimeter and the outer diameter $D_2$ is generally no larger than 11 millimeters for use in a human eye. The entire film is perforated throughout with the pores 2, which are drawn grossly oversized and sparsely distributed in FIG. 1 for illustration purposes. The widths of the pores 2 shown in FIG. 1 are preferably 0.005 to 15 microns which, as taught by Steele, et. al., is the appropriate width range to allow for the flux of tissue fluid components whilst excluding the ingrowth of ocular tissue. Neither the term pore nor the drawing in FIG. 1 is meant to imply any geometric restriction on the shape of the pore openings, which are in general irregular. Neither are the pores all of the same width, but vary in width within a range determined by the production method. The area of the film 5 external to the iris pattern constitutes the skirt of the device, which may be utilized for surgical positioning and anchoring purposes. As shown in FIG. 1, the pores in the skirt may be made wider than those in the iris region to allow for ocular tissue ingrowth to occur in the skirt, which may help to anchor the artificial iris in the eye.

The remaining figures and descriptions consider realizations of the artificial iris without the skirt 5 shown in FIG. 1. The skirt may be separated from the pupillary core that contains the iris at any stage of processing by using a trephine similar to that used in the preparation of corneal donor tissue. The trephine may be heated to cleanly cut the polymer. FIG. 2 provides a cross-sectional view taken generally along the line A-A in FIG. 1, with the skirt 5 removed, of the product of the first embodiment of the artificial iris. The thickness T of the artificial iris indicated in FIG. 2 is typically 5-10 microns but may be up to 20 microns or as thin as 1 micron. The imprinted annulus bounded in FIG. 2 by the edges 3 and 4 is, in the first embodiment of the artificial iris, a buried layer of an opaque material such as graphite that provides opacity to light of all colors throughout the optical spectrum. In the embodiment depicted in FIG. 2, the buried layer material is concentrated generally at 6 in the middle of the polymer film and becomes less concentrated in layers closer to the film surface. This feature of the artificial iris provides flexibility, durability, and prevents fragmentation of the opaque material during surgical handling and applications of stress to the eye. FIG. 2 also depicts the pores 2, which again are drawn grossly oversized and sparsely distributed for illustration purposes, which perforate the film to provide for the flux of tissue fluid components through the artificial iris.

FIGS. 3-8 and the accompanying descriptions deal with the method of production of the first embodiment of the artificial iris through the use of polymer processing and irradiation techniques. To this end FIGS. 3-8 depict the first embodiment of the artificial iris in intermediate forms at progressive stages in the production process. FIGS. 9-10 and the accompanying text then describe the artificial iris of the second embodiment of the invention, which features a partially reflective iris, and the method of production of this embodiment through the use of laser irradiation. Intermediate forms and stages of the first embodiment of the artificial iris that also occur in the second embodiment are cited accordingly.

The initial procedure in the production process of all embodiments of the invention is the formation of a polymer film of the desired thickness on a suitable substrate. This is accomplished using established techniques of spin-coating the selected polymer from solution, as are described for instance by Wolf and Tauber in the context of photoresists for microelectronics processing. The polymer is cast onto the substrate to a nominal thickness of 7-15 microns. A thickness greater than that of the finished artificial iris (T in FIG. 2) is required because the film will contract when irradiated during subsequent processing. The uniform polymer film is then exposed to either an optical lithography source, such as but not limited to an excimer laser, or an ion-beam lithography source, such as but not limited to a proton beam, through a standard binary shadow or stencil mask, respectively. For the specific case of the artificial iris the shadow or stencil mask is simply a hole of diameter $D_1$ in an otherwise opaque mask, through which a single exposure is performed, however in other embodiments of the corneal implant the mask may be more detailed or adjustable and may be reoriented or adjusted throughout a series of exposures. Ion beam lithography has the benefit of optional dry processing that enables the stencil mask to be rigidly attached in contact with the polymer film.

Following exposure through the shadow or stencil mask, development of the polymer film in a suitable solvent yields the surface-relief structure depicted in FIGS. 3 and 4. The surface-relief structure is formed without development if dry ion beam lithography is used. FIG. 3 is a front-view depiction of the polymer surface-relief structure, which for the first embodiment of the artificial iris is in the form of a disk 10 of diameter $D_2$ with a concentric circular inset 11 of diameter $D_1$. The disk is transparent and is shown in FIG. 3 in contrast to the substrate 12 for illustration purposes only. FIG. 4 is a cross-sectional view taken generally along the line B-B in FIG. 3. As indicated in FIG. 4 the substrate is composed of a rigid base material 12, which is for example silicon, and optionally a release layer 13, which is for example silicon dioxide. The release layer 13 may be required to free the implant from the substrate at the completion of processing, in which case a conventional etchant, for example hydrofluoric acid, dissolves the release layer 13 but not the base 12 or the processed implant. The processed implant can usually be manually lifted from the substrate following treatment in a suitable solution, for example, processed PMMA can be lifted from a glass substrate after soaking in a potassium hydroxide solution. As depicted in FIG. 4, in the artificial iris embodiment the polymer surface-relief structure is composed of the disk or outer band 10 that is nominally 7-15 microns thick (vertical in FIG. 4) and $(D_2-D_1)/2$ wide in cross-section and is bounded by the ideally vertical cylindrical walls 14 and 15, and the circular inset 11 that is nominally 5-10 microns thick and $D_1$ wide in cross-section. Still referring to FIG. 4, the band 10 is purposefully thicker than the circular inset 11 because the band is exposed to heavier irradiation during subsequent processing and therefore experiences more contraction. The surface-relief pattern of the structure shown in FIG. 4 compensates for the differential contraction in the two regions, which results in a uniformly thin implant at the completion of processing. The exact height of the cylindrical wall 15 is determined by the differential contraction of the band 10 and the inset 11 during subsequent processing by ion or laser irradiation. The surface-relief pattern is more varied for other embodiments of the invention, for instance in the form of a concave dome for a cornea reshaping implant designed to correct for hyperopia or a concave impression for a cornea reshaping implant designed to correct for myopia.

FIG. 5 depicts irradiation of the polymer surface-relief structure of FIGS. 3 and 4 by a uniform, diffuse beam 16 of ions or x-rays to form the pores of the artificial iris. The beam 16 may also be in the form of a directed flood beam or a confined beam that is raster-scanned over the film, but the diffuse beam is preferable because it generates more pore volume in the film, which facilitates tissue fluid flow through percolation. According to Steele, et. al. the pores are preferably 0.005 to 15 microns wide with a surface density of 200 to 300,000 pores per square millimeter to allow for the adequate flow of tissue fluid components through the implant. The surface density of the pores is proportional to the radiation dose, while the pore width is largely determined by a subsequent etching process. High-energy ions form ion-tracks in polymers that yield pores when suitably etched. For instance, as demonstrated by Trautmann, et. al., approximately 0.5-micron wide circular pores can be produced throughout 50-micron thick PI by irradiating the polymer with krypton ions with energies of around 860 million electron volts (eV) and etching the irradiated film in chlorine bleach for 7 hours. Lower energies and shorter etching times are required for thinner films. The dependence of pore width on etch time in several irradiated polymer films is known from the results of Ferain and Lergas. An ion beam capable of forming ion tracks that can be subsequently etched into pores may be generated by a high-voltage ion accelerator such as but not limited to a tandem Van de Graff accelerator or a cyclotron. As demonstrated by Valiev, et. al., x-rays in the wavelength range $\lambda=0.8$-3.0 nanometers produce minute pores around 0.003 microns wide in PMMA without a subsequent etching step, although appropriate etching will widen the pores so produced.

In the process of the first embodiment of the artificial iris the latent tracks or pores produced by the irradiation depicted in FIG. 5 may not be etched immediately, rather the processes required to form the opaque iris pattern may be performed before pore etching.

Allowance should also be made for the process of pore-etching prior to iris pattern formation and for the high-energy ion irradiation and subsequent etching responsible for pore formation to be performed after the iris pattern is formed. Assuming for further description that the polymer film contains latent pores, first a protective metal layer is deposited over the circular inset 11 as depicted in FIG. 6. The stencil 17, which is in the form of an annulus with an outer diameter larger than $D_2$ and an inner diameter slightly smaller than or equal to $D_1$, is placed concentric with the circular inset 11 directly on top of the polymer surface-relief structure. The metal atoms 18 in the deposition chamber tend to undercut the stencil and form a protective layer similar to that depicted at 19 in FIG. 6.

FIG. 7 depicts a uniform, directed flood beam of ions 20 irradiating the polymer surface-relief structure to form the opaque iris pattern, with the pupil protected by the metal layer 19. An alternative to form the opaque iris pattern, which is illustrated in FIG. 8, utilizes a stencil mask made of a suitable material and comprising an inner circular disk 21, an annular clearance 22, and a support flange 23 situated in front of the polymer structure in order to project a shadow in the shape of a circular disk onto the inset 11 and thereby irradiate the polymer structure in the annular pattern 24, shown in cross-section in FIG. 8, that coincides with the band 10 in the polymer structure. If the irradiation process depicted in FIG. 8 is used to form the iris pattern, then pore-etching can be done before the iris pattern generation or vice versa. In the irradiation process depicted in either FIG. 7 or FIG. 8 the desired buried layer that forms the opaque iris pattern may, for example, be produced by a beam of medium-energy (300 thousand eV) argon ions applied to a dose of one thousand trillion ions per square centimeter, which in PMMA forms a buried graphite layer centered at a depth of around 3 microns beneath the surface. Such an ion beam may be produced by ion implanters commonly employed in the microelectronics industry. The quoted energy and depth figures are calculated using the TRIM simulation code of Ziegler and Biersack. The opacity of the buried iris pattern may be adjusted by changing either the ion energy or dose. The irradiation that generates the buried iris pattern also results in contraction of the polymer film to the extent that the post-irradiation thickness of the band 10 equals that of the protected inset 11, resulting in a smooth, planar processed film and implant.

The second embodiment of the artificial iris provides an annular iris region composed of layers of alternating refractive index with depth, thus forming a reflective or Bragg diffraction grating that selectively reflects a predetermined range of colors while transmitting all other colors. FIG. 9 depicts a cross-sectional view of the artificial iris of the second embodiment of the invention taken similarly to that of FIG. 2. The properties of the second embodiment of the artificial iris are identical to those of the first embodiment of the artificial iris depicted in FIG. 2 except that the buried opaque layer of the latter (6 in FIG. 2) is replaced in the former by the series of alternating refractive-index layers indicated by 25 in FIG. 9. The alternating refractive-index layers indicated by 25 in FIG. 9 may be of fixed or variable thickness. Such a series of alternating refractive-index layers forms a reflective or Bragg diffraction grating, the optical properties of which are indicated schematically in FIG. 9 for a particular realization by the arrows or rays 26, 27, and 28. The annotations R, G, and B on the rays 26, 27, and 28 denote red, green, and blue light, respectively. As depicted in FIG. 9, white light indicated by ray 26 incident on a particular realization of the Bragg grating 25 is split into a blue reflected component, which is indicated by ray 27, and a red-green transmitted component, which is indicated by ray 28. In reality the reflected light falls in a continuous color band around a central color, with the central color and the bandwidth determined by the spacing and the number of the refractive-index layers in the Bragg grating 25, respectively. The incidence angle $\theta$ in FIG. 9 over which the Bragg grating 25 performs is also determined by the number of refractive-index layers and is generally limited to less than the acceptance angle of the eye, which is $\pm 7°$ as measured from the normal line 29 in FIG. 9. The central color, bandwidth, and performance angle of the Bragg grating 25 in FIG. 9 are adjustable through the production processes of the second embodiment of the artificial iris. In this embodiment the artificial iris serves one opthalmological function in the reflected color band and another opthalmological function in the transmitted color band. Specifically, in the application of refractive-error compensation the compensation occurs in the reflected color band while low-light vision occurs primarily in the transmitted color band.

The production process of the second embodiment of the artificial iris follows that of the first embodiment through the processing steps depicted in FIGS. 3-5 and described in the accompanying text. The pores 30 in FIG. 9 are similarly generated in the second embodiment in accordance with the description that accompanies FIG. 5, and the latent tracks or pores may be etched immediately, prior to formation of the Bragg grating in the iris pattern. The Bragg grating of the artificial iris is formed by laser irradiation in the configuration illustrated in FIG. 10. Depicted in FIG. 10 is a collimated flood laser beam 31, generated by a source such as but not limited to an excimer laser, incident on the polymer structure depicted in FIGS. 3-4 through a binary shadow mask composed of an opaque circular disk 32 on an appropriate substrate 33 of a material such as but not limited to quartz, with the disk 32 ideally perfectly aligned with the circular inset of the polymer structure indicated by 11 in FIGS. 3-4. The polymer structure of FIGS. 3-4 is drawn grossly oversized in FIG. 11 for illustration purposes. On the side of the polymer structure opposite the laser source is a mirror 34 that reflects the laser light back through the polymer structure such that an interference fringe pattern 35 is formed within the outer band of the polymer structure indicated by 10 in FIG. 4. Through photochemical reaction the interference fringe pattern is transferred to a set of modified refractive-index layers, which as shown in FIG. 10 are generally ideally parallel to the surface of the polymer structure but may also be made slanted relative to the surface of the polymer structure by tilting the mirror 34, and which form the Bragg grating of the second embodiment of the artificial iris. The substrate 36 in FIG. 10 must be either transparent to the laser radiation 31 or serve as a mirror to reflect the laser radiation 31 back into the polymer structure for the formation of a Bragg grating in the iris pattern with interference fringes parallel to the polymer film surface, in which case the external mirror 34 is unnecessary.

Whereas the drawings and accompanying description have shown and described the artificial iris embodiment of the current invention, it should be apparent to those skilled in the art that various changes may be made in the form of the invention without affecting the scope thereof.

I claim:
1. A method of forming an optical device for surgical insertion into the cornea of an eye as a corneal implant, said method including the steps of:
  a. providing a polymer film having first and second surfaces;
  b. forming tracks in said polymer film by exposing said polymer film to a first source of radiation;
  c. etching said tracks to form at least some pores in said polymer film which connect said first and second surfaces;
  d. widening by etching at least some of said pores to dimensions large enough to permit the ingrowth of corneal tissue;
  e. providing a first mask; and
  f. reducing the transmission of at least a first portion of said polymer film to at least certain wavelengths of visible light by exposing said first portion of said polymer film to a second source of radiation through said first mask to produce the corneal implant
  wherein said step of reducing said transmission is achieved by the step of forming a diffraction grating designed to reflect pre-selected wavelengths of visible light while transmitting other wavelengths.
2. A method of forming an optical device for surgical insertion into the cornea of an eye as a corneal implant, said method including the steps of:
  a. providing a polymer film having first and second surfaces;
  b. forming tracks in said polymer film by exposing said polymer film to a first source of radiation;
  c. etching said tracks to form at least some pores in said polymer film which connect said first and second surfaces;
  d. providing a first and a second mask;
  e. reducing the transmission of at least a first portion of said polymer film to at least certain wavelengths of visible light by exposing said first portion to a second source of radiation through said first mask; and
  f. forming surface relief in said polymer film by exposing a second portion of said polymer film to a third source of radiation through said second mask to produce the corneal implant.
3. The method of claim 2, wherein the step of reducing said transmission with said second source of radiation is achieved by using a source of accelerated ions to form a buried partly- to fully-opaque layer in said first portion of said polymer film.
4. The method of claim 2, wherein the step of forming said tracks with said first source of radiation is achieved by using a source of accelerated ions.
5. The method of claim 2, wherein the step of forming said tracks with said first source of radiation is achieved by using a source of x-rays.
6. The method of claim 2, wherein said step of forming said surface relief with said third source of radiation includes the step of forming within said polymer film a central disc and a concentric annulus of different thickness.
7. The method of claim 2, wherein the step of forming said surface relief with said third source of radiation includes the step of producing surface relief within said polymer film designed to correct for refractive error in an eye.
8. The method of claim 2, wherein said third source of radiation is selected from the group including optical lithography sources and ion beam sources.
9. The method of claim 6, wherein said step of reducing transmission is achieved by the step of exposing said concentric annulus to a source of accelerated ions to form a buried partly- to fully-opaque layer in said concentric annulus.
10. A method of forming an optical device for surgical insertion into the cornea of an eye as a corneal implant, said method including the steps of:
  a. providing a polymer film having first and second surfaces;
  b. forming tracks in said polymer film by exposing said polymer film to a first source of radiation;
  c. etching said tracks to form at least some pores in said polymer film which connect said first and second surfaces;
  d. widening by etching at least some of said pores to dimensions large enough to permit the ingrowth of corneal tissue;
  e. providing a first and a second mask;
  f. reducing the transmission of at least a first portion of said polymer film to at least certain wavelengths of visible light by exposing said first portion to a second source of radiation through said first mask; and
  g. forming surface relief in said polymer film by exposing a second portion of said polymer film to a third source of radiation through said second mask to produce the corneal implant,
  wherein said step of forming said surface relief with said third source of radiation includes the step of forming within said polymer film a central disc and a concentric annulus of different thickness and wherein said step of reducing transmission is achieved by the step of forming within said concentric annulus a diffraction grating designed to reflect pre-selected wavelengths of visible light while transmitting other wavelengths.

* * * * *